United States Patent [19]

Schilling, Jr.

[11] Patent Number: 5,082,962

[45] Date of Patent: Jan. 21, 1992

[54] STERICALLY HINDERED AMINOHYDROCARBYLSILANES AND PROCESS OF PREPARATION

[75] Inventor: Curtis L. Schilling, Jr., Croton-on-Hudson, N.Y.

[73] Assignee: Union Carbide Chemicals and Plastics Technology Corporation, Danbury, Conn.

[21] Appl. No.: 651,557

[22] Filed: Feb. 6, 1991

Related U.S. Application Data

[62] Division of Ser. No. 529,400, May 29, 1990, Pat. No. 5,030,746.

[51] Int. Cl.$^5$ .............................. C07F 7/04; C07F 7/08
[52] U.S. Cl. ........................ 556/479; 556/410; 556/413; 556/435; 556/466; 556/482; 556/484; 556/486
[58] Field of Search ............... 556/410, 413, 435, 466, 556/482, 484, 486, 479

[56] References Cited

U.S. PATENT DOCUMENTS

| | | | |
|---|---|---|---|
| 2,557,803 | 6/1951 | Sommer | 260/448.2 |
| 2,832,754 | 4/1958 | Jex et al. | 260/46.5 |
| 2,971,864 | 2/1961 | Speier | 117/124 |
| 3,146,250 | 8/1964 | Speier | 260/448.2 |
| 3,657,303 | 4/1972 | Golltz et al. | 260/448.2 |
| 3,673,233 | 6/1972 | Golltz et al. | 260/448.2 |
| 3,810,843 | 5/1974 | Slusarczuk et al. | 252/313 |
| 4,481,364 | 11/1984 | Chu et al. | 556/413 |

OTHER PUBLICATIONS

J. Org. Chem. 35, 3879 (1970).
J. Org. Chem. 36, 3120 (1971).
J. Gen. Chem. (USSR) 40, 595 (1970); 41, 1591 (1971); 45, 81 (1975); 46, 2074 (1976); 51, 311 (1981).

*Primary Examiner*—Jose G. Dees
*Assistant Examiner*—Porfirio Nazario
*Attorney, Agent, or Firm*—Bonnie L. Deppenbrock

[57] ABSTRACT

Novel silanes having sterically hindered aminohydrocarbyl groups of the formula $X_3SiRCR'_2NR''_2$ and having utility as coupling agents and a process for their preparation are described.

9 Claims, No Drawings

STERICALLY HINDERED AMINOHYDROCARBYLSILANES AND PROCESS OF PREPARATION

This application is a division of prior U.S. application Ser. No. 529,400, filing date May 29, 1990, now U.S. Pat. No. 5,030,746.

BACKGROUND OF THE INVENTION

1. Field of the Invention

This invention relates to novel silanes having sterically hindered aminohydrocarbyl groups and to a process for their preparation. The sterically hindered aminohydrocarbylsilanes of this invention find general utility as glass-plastic coupling agents, bonding aids, consolidating additives to phenolic binder/foundry mixtures, and adhesion promoters for vinyl plastisols, polyurethane elastomers, and epoxy and acrylic-based inks.

2. The Prior Art

3-Aminopropyl silanes, containing the moiety $\equiv SiCH_2CH_2CH_2N=$, have long been articles of commerce. While fairly extensive prior art exists on making such materials and in varying the substituents on either the silicon atom or the nitrogen atom in such materials, relatively little has been done on varying the linkage between the silicon and nitrogen atoms. Thus, for example, there is prior art on a single carbon linkage between silicon and nitrogen atoms (U.S. Pat. Nos. 3,657,303 and 3,673,233), on two carbon linkages (U.S. Pat. No. 2,557,803), on four carbon linkages (U.S. Pat. No. 3,146,250), and even on eleven carbon linkages (U.S. Pat. No. 3,810,843). Even less has been done on varying the carbon linkage from linear to branched or cyclic, although prior art exists on the moieties $\equiv SiCHMeCH_2N=$ (J. Org. Chem., 35, 3879 (1970)), $\equiv SiCH_2CHMeCH_2N=$ (J. Org. Chem., 36, 3120 (1971), and certain cyclic linkages (U.S. Pat. No. 2,762,823).

A limited amount of work has also been done on preparing unsaturated two and three carbon linkages on silyl tertiary amines (J. Gen. Chem. (USSR), 40, 595 (1970), 41, 1591 (1971), 45, 81 (1975), and 51, 311 (1981)). Another unsaturated silyl tertiary amine with the moiety $\equiv SiCH_2CH=CHN=$ is disclosed in J. Gen. Chem. (USSR), 46, 2074 (1976). The compound $(MeO)_3SiCH=CHCH_2NHCH_2CH_2NH_2$ is disclosed in U.S. Pat. No. 2,971,864 (Example 3). None of the above references disclose sterically hindered aminohydrocarbylsilanes.

OBJECTIVES OF THE INVENTION

It is an object of the present invention to prepare sterically hindered aminohydrocarbylsilanes (particularly aminoalkyl or aminoalkenylsilanes).

It is a further object of the present invention to provide a process for preparing sterically hindered aminohydrocarbylsilanes via hydrosilation or sequential hydrosilation/ hydrogenation or hydrogenation/hydrosilation reactions between silanes having silicon-bonded hydrogen groups and sterically hindered amines with acetylenic or olefinic unsaturation.

It is still another object of the present invention to provide sterically hindered aminohydrocarbylsilanes (particularly aminoalkyl or aminoalkenylsilanes) useful in applications in which aminopropylsilanes are useful but with the advantage of providing amine groups differing in reactivity and basicity from the aminopropylsilanes.

SUMMARY OF THE INVENTION

The present invention provides sterically hindered aminohydrocarbylsilanes having the formula:

$$X_3SiRCR'_2NR''_2 \qquad (I)$$

R is a linear or branched, saturated or unsaturated divalent hydrocarbon group having 2 to 12 carbon atoms. R' is an alkyl group having 1 to 8 carbon atoms or an aryl group having 6 to 12 carbon atoms. R" is a hydrogen, an alkyl group having 1 to 8 carbon atoms, an aryl group having 6 to 12 carbon atoms, or a silyl group ($-SiX'_3$, wherein X' is an alkyl group having 1 to 3 carbon atoms, preferably a methyl group). The two R' groups can be the same or different in any given compound. Likewise, the two R" groups can be the same or different. X is an alkyl group having 1 to 8 carbon atoms, an aryl group having 6 to 12 carbon atoms, an alkoxy group having 1 to 8 carbon atoms, an aryloxy group having 6 to 12 carbon atoms or a halogen atom. Each X can be the same or different in any given compound.

The invention also provides a process for preparing sterically hindered aminohydrocarbylsilanes which comprises reacting a hydrosilane having the formula

$$X_3SiH \qquad (II)$$

with a sterically hindered unsaturated amine having the formula

$$R'''CR'_2NR''_2 \qquad (III)$$

In formula II, X is as defined in formula I. In formula III, R' and R" are as defined in formula I. R''' is a monovalent acetylenic ($-C\equiv CR''$) or vinylic ($-CH=CH_2$) group. The hydrosilane and the amine are reacted in the presence of a noble metal catalyst at an elevated temperature.

DETAILED DESCRIPTION OF THE INVENTION

These novel silanes are prepared by hydrosilation reactions of silanes having silicon-bonded hydrogen groups with sterically hindered amines containing either acetylenic or olefinic unsaturation as follows:

(a) $R''C\equiv CCR'_2NR''_2 + X_3SiH \xrightarrow{catalyst} X_3SiRCR'_2NR''_2$ \qquad (IV)

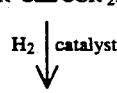

$H_2$ | catalyst

(b) $R''HC=CHCR'_2NR''_2 + X_3SiH \xrightarrow{catalyst} X_3SiRCR'_2NR''_2$

R, R', R" and X are as defined in Formula I. When R" on the terminal acetylenic carbon is H (hydrogen), the sterically hindered amine reactants can be hydrogenatively reduced to the respective olefinic amines.

The hydrosilation reactions of the present invention proceed with almost exclusive formation of a single isomeric unit, i.e., the silicon atoms become attached to the terminal carbon atoms of terminally unsaturated sterically hindered amines.

The hydrosilation reactions of acetylenic sterically hindered amines proceed at higher rates when the amine group is silyl-capped, i.e., one of the R" is a silyl group such as —SiX'$_3$ where X' is an alkyl group, having 1 to 3 carbon atoms, preferably a methyl group. Such silyl capping groups can be easily replaced by hydrogen through treatment of the silane with methanol (before or after hydrogenation) as illustrated below:

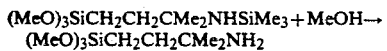

The acetylenic and olefinic sterically hindered amine reactants include compounds having the structures represented by formula III and more specifically represented by:

(V)

wherein R' is an alkyl group of 1 to 4 carbon atoms, and R" is a hydrogen atom (preferred), alkyl or aryl group, or silyl group (i.e., —SiX'$_3$ with —SiMe$_3$ being preferred).

The acetylenically unsaturated sterically hindered amines useful in the present invention can be converted to the olefinically unsaturated sterically hindered amines, also useful in the present invention, by hydrogenative reduction with specific catalysts for such reductions such as the Lindlar ™ catalyst. Specific examples include: HC≡CCMe$_2$NH$_2$ CH$_2$=CHCMe$_2$NH$_2$ HC≡CCMe$_2$NHSiMe$_3$ CH$_2$=CHCMe$_2$NHSiMe$_3$ φC≡CCMe$_2$NH$_2$ MeC≡CCMe$_2$NHSiMe$_3$ HC≡CCMe$_2$NHSiMe$_2$H CH$_2$=CHCMe$_2$NHSiMe$_2$H HC≡CCMe$_2$NHMe HC≡CCMe$_2$N(SiMe$_3$)$_2$. HC≡CCMe$_2$NH$_2$ and its derivatives (either reduced and/or silylated) are preferred reactants in the process of the present invention for reasons of reactivity and commercial availability. HC≡CCMe$_2$NH$_2$ is commercially available and does reduce to CH$_2$=CHCMe$_2$NH$_2$.

The silanes having silicon-bonded hydrogen groups used in the Process of this invention are well known in the art and generally include those capable of undergoing hydrosilation reactions. These silanes have the formula X$_3$SiH where X is as defined above in formula I (with the proviso that such a halosilane should be unreactive with the sterically hindered amine group). More specifically, the silane may include the halosilanes having the formula R$_x$SiY$_{3-x}$H where Y is a halogen, preferably chlorine, the alkoxysilanes having the formula R$_x$Si(OR)$_{3-x}$H where R is an alkyl group of 1 to 4 carbon atoms, preferably a methyl group, or an aryl group having 6 to 12 carbon atoms, preferably Phenyl, and x is an integer ranging from 0 to 3. Specific examples include: Cl$_3$SiH MeSiHCl$_2$ Me$_2$SiHCl Me$_3$SiH Et$_3$SiH EtSiHCl$_2$ φSiHCl$_2$ (MeO)$_3$SiH (EtO)$_3$SiH Me(MeO)$_2$SiH Me$_2$Si(OMe)H Me$_2$Si(OEt)H φSi(OMe)$_2$H and the like.

In the practice of the process of this invention, acetylenic or olefinic sterically hindered amines and the silanes having silicon-bonded hydrogen as described above can be reacted in the same manner as unhindered, unsaturated amines and hydrosilanes are reacted in conventional hydrosilation reactions. A noble metal may be employed as a catalyst in the process of the present invention. Thus, preferably, for example, various forms and derivatives of platinum metal may be used as catalysts in this invention. Most preferred are solutions or derivatives of chloroplatinic acid for use as catalysts in the process of the invention. The reaction of these components is illustrated as follows:

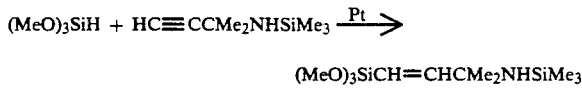

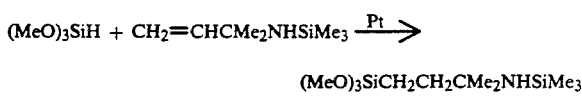

In the practice of the present invention, the reaction between the silane and the amine is conducted at an elevated temperature, preferably from about 50° C. to 160° C., and most preferably from about 80° C. to 140° C. Further, the reaction is conducted at atmospheric pressure since no obvious advantage occurs at higher pressures.

The products deriving from acetylenic sterically hindered amines are almost exclusively single isomers, contrary to prior art on acetylenic tertiary amines, with the silicon moieties becoming bonded to the terminal carbon atoms of the acetylenic groups. These products, which are themselves olefinically unsaturated, can be converted to saturated Products (which are otherwise directly obtainable by hydrosilation of olefinic sterically hindered amines) by simple hydrogenative reduction, for example,

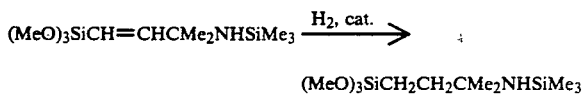

The silyl groups on nitrogen are removable by simple treatment with methanol.

The choice of unsaturated versus saturated products may be made on the grounds of the basicity desired for the product. The saturated products are estimated to be more basic by about 0.5 PK unit, based on data by Campbell, et al., *Journal of Organic Chemistry*, Volume 17, 1141 (1962), for related sterically hindered amines. The residual double bond in the unsaturated product also provides an additional reactive site which can be used, for example, in curing or crosslinking by addition of free radicals.

The processes of the present invention are not narrowly limited with regard to equipment size, reaction time, temperature, heat, pressure, or solvents.

Thus, the silanes having sterically hindered amine groups of the present invention are useful in the same application areas as 3-aminopropyl silanes. However, these silanes having sterically hindered amine groups of the present invention differ in reactivity and basicity compared to 3-aminopropyl silanes that are currently available. While silanes that do not have sterically hindered amine groups, such as 3-aminopropyl silanes, react with aldehydes or ketones to form imines, the silanes of the present invention do not react and, therefore, can be used as solutions in acetone. Further, when silanes having sterically hindered amine groups are employed in applications in which 3-aminopropyl silanes have been used, such as in fiberglass reinforced composites, improvement is noted in, for example, flexural strength and abrasion resistance.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLES

All reactions were run in standard laboratory glassware of various sizes using heating mantles, mechanical or magnetic stirrers, thermometers, condensers, and provisions for maintenance of nitrogen atmospheres. Temperatures are recorded in Centigrade degrees, and the abbreviations g., mm., ml., min., hr., lb., and psi represent gram, millimeter, milliliter, minute, hour pound and pounds per square inch, respectively. Also, Me represents methyl and $\phi$ represents phenyl.

Procedure 1—Drying of HC≡CCMe$_2$NH$_2$

Commercially available HC≡CCMe$_2$NH$_2$ contains about 10% water as received. The water content is reduced by the addition of sodium hydroxide pellets. The pellets slowly dissolve, causing separation of a dense lower phase consisting of an aqueous solution of sodium hydroxide. Removal of the lower phase leaves HC≡CCMe$_2$NH$_2$ containing <1% water, which can be used as is, or dried further by traditional drying agents. Thus, treatment of 163.9 g of commercial HC≡CCMe$_2$NH$_2$ with 31.1 g NaOH pellets with magnetic stirring and standing overnight, following by removal of the lower phase, provided amine with 0.71% H$_2$O.

Procedure 2—Reduction of HC≡CCMe$_2$NH$_2$ to CH$_2$=CHCMe$_2$NH$_2$

In the bottle of a standard Parr hydrogenation apparatus were combined 52.0 g of HC≡CCMe$_2$NH$_2$ dried in the same manner as in Procedure 1, 50.0 g of tetrahydrofuran solvent, and 0.21 g of catalyst (5% Pd on CaCO$_3$). Bottle was pressurized to 59 psi at 20°, and heated to 38° while shaking. Pressure dropped to 13 lb in 3 hr; system was repressurized to 60 lb and allowed to stand overnight. Analysis by nuclear magnetic resonance (NMR) showed that the acetylenic groups had been converted to vinylic groups, i.e., the desired product, CH$_2$=CHCMe$_2$NH$_2$, was obtained.

Procedure 3—Preparation of HC≡CCMe$_2$NHSiMe$_3$

In 5000 ml flask were combined 250 g of commercial HC≡CCMe$_2$NH$_2$, 581.8 g of triethylamine, and 1637.5 g of tetrahydrofuran solvent. The flask and contents were cooled at 17° and addition of 625.5 g of trimethylchlorosilane begun with rapid stirring under nitrogen. The addition was completed in 90 min, followed by stirring for 85 min. Analysis by gas chromatography (GC) showed a small amount of HC≡CCMe$_2$NH$_2$, which was converted to product by an additional 53.4 g of trimethylchlorosilane. Reaction mixture was pressure-filtered and the solids triturated with fresh tetrahydrofuran and refiltered. The organic solutions were combined and distilled, providing the desired product, HC≡CCMe$_2$NHSiMe$_3$, as a liquid boiling at 135° at atmospheric pressure. Its structure was confirmed by NMR analysis.

Procedure 4—Preparation of CH$_2$=CHCMe$_2$NHSiMe$_3$

Procedure 3 was followed with 75.7 g of CH$_2$=CHCMe$_2$NH$_2$ prepared by procedure 2. The desired product, CH$_2$=CHCMe$_2$NHSiMe$_3$, was obtained as a liquid boiling at 140°. Its structure was proven by NMR analysis.

Comparative Example A—Reaction of HC≡CCMe$_2$NH$_2$ with (MeO)$_3$SiH

In a 250 ml flask were combined 57.4 g of toluene solvent, 40.0 g of dried HC≡CCMe$_2$NH$_2$, and 49.5 g of (MeO)$_3$SiH. Heat was applied to reflux and several droplets of chloroplatinic acid solution (4 wt-% in MeOCH$_2$CH$_2$OMe) added. Heating at reflux was continued for 18 hr and the reaction mixture distilled, yielding 1.6 g of (MeO)$_3$SiCH=CHCMe$_2$NH$_2$, boiling at 60°/1 mm. This examples shows that the reaction of (MeO)$_3$SiH with HC≡CCMe$_2$NH$_2$ is very slow at atmospheric pressure and low reflux temperature (91°-3°). The product was identified by NMR analysis.

Example 1—Reaction of HC≡CCMe$_2$NHSiMe$_3$ with (MeO)$_3$SiH

The procedure of Example A was followed in a 25 ml apparatus using 7.4 g of (MeO)$_3$SiH, 8.6 g of HC≡CCMe$_2$NHSiMe$_3$ (prepared by procedure 3), and two droplets of platinum catalyst solution. Heat was applied, with the reflux temperature continuously rising to 143° over 2 hr. Vacuum distillation provided 2.8 g (83.8% yield) or (MeO)$_3$SiCH=CHCMe$_2$NHSiMe$_3$ boiling at 87°/2 mm, its structure confirmed by NMR analysis. When contrasted with Comparative Example A this example shows that (MeO)$_3$SiH reacts much more rapidly with the silyl-capped amine, HC≡CCMe$_2$NHSiMe$_3$, than it does with the uncapped amine, HC≡CCMe$_2$NH$_2$, under atmospheric reflux conditions.

Example 2—Preparation of (MeO)$_3$SiCH=CHCMe$_2$NH$_2$

The Product of Example 1 was stirred with an equal volume of MeOH at room temperature. The uncapped product, (MeO)$_3$SiCH=CHCMe$_2$NH$_2$, was isolated by distillation at 60°/0.8 mm in quantitative yield as the trans-terminal isomer, based on NMR, virtually identical to the Product of Example A.

Example 3—Reduction of (MeO)$_3$SiCH=CHCMe$_2$NHSiMe$_3$

Product prepared for Example 1, 70.3 g, was combined with 20 g of petroleum ether in the bottle of a standard Parr hydrogenation apparatus. Catalyst (0.7 g of 5% Pd/CaCO$_3$, corresponding to 500 parts per million) was added and the system pressurized to 75 psi with hydrogen, followed by heating to 50° while shaking over 90 min. NMR Analysis showed no residual unsaturation. The desired product, (MeO)$_3$SiCH$_2$CH$_2$CMe$_2$NHSiMe$_3$, was isolated by distillation at 80°/1 mm, and its structure proven by NMR analysis.

Example 4—Preparation of (MeO)$_3$SiCH$_2$CH$_2$CMe$_2$NH$_2$

The product of Example 3, as undistilled and distilled separate samples, was treated with MeOH per Example 2. Distillation of both provided (MeO)$_3$SiCH$_2$CH$_2$-

$CMe_2NH_2$ in essentially quantitative yields at 60°/0.8 mm, with structure confirmed by NMR analysis.

Example 5—Reaction of $(MeO)_3SiH$ with $CH_2=CHCME_2NHSiMe_3$ and Preparation of $(MeO)_3SiCH_2CH_2CMe_2NH_2$ The reaction of Example 1 was repeated except that $CH_2=CHCMe_2NHSiMe_3$ was used in place of $HC\equiv CCMe_2NHSiMe_3$. The product, $(MeO)_3SiCH_2CH_2CMe_2NHSiMe_3$, was isolated by distillation at 79°/1.5 mm, and was identical to the Product of Example 3. Treatment of the product of the instant example per the procedure of Example 4 provided product identical to that of Example 4, i.e., $(MeO)_3SiCH_2CH_2CMe_2NH_2$. This example shows that product can be prepared by a sequence of hydrosilation and reduction reactions, or a sequence of reduction and hydrosilation reactions, both beginning with $HC\equiv CCMe_2NH_2$ and involving intermediate silyl capping steps.

Example 6—Reaction of $(MeO)_3SiH$ with $CH_2=CHCMe_2NH_2$

The reaction of Example A was repeated except that $CH_2=CHCMe_2NH_2$ was used in place of $HC\equiv CCMe_2NH_2$. Addition of catalyst at 78° caused an exotherm of 125° in a few minutes. Distillation provided the desired product at 42°/0.95 mm, with structure confirmed by NMR analysis. This example shows that silyl capping of $CH_2=CHCMe_2NH_2$ is not necessary to achieve good yields and high reaction rates.

Procedure 5—Preparation of $H_2C=CHCMe_2NH_2$

The product (375.6 g) prepared according to Procedure 1 was combined with 300 g of petroleum ether in a 3 1 Bomb from a Parr rocker type reactor. Catalyst (1.2 g of 5% $Pd/CaCO_3$, lead-poisoned, corresponding to 200 parts per million) was added and the system was pressurized to 1100 psi with hydrogen. The reaction vessel was shaken. The reaction temperature increased to 212° in 4 minutes, along with a pressure drop to 150 psi. The reaction vessel was shaken for an additional 3.5 hr. The product structure was confirmed by NMR analysis.

Example 7—Preparation of $(MeO)_3SiCH_2CH_2CMe_2NH_2$

In a 1000 ml flask 850.1 g of $H_2C=CHCMe_2NH_2$/petroleum ether mixture (prepared according to Procedure 5), was added and heat applied to reflux. At 49° 1.8 ml chloroplatinic acid solution (corresponding to 213 parts per million platinum) was added while stirring rapidly under nitrogen. $(MeO)_3SiH$ (692 g) was added in 3.5 hr with the reflux temperature continuously rising to 58°. Analysis by gas chromatography (GC) showed unreacted $H_2C=CHCMe_2NH_2$, an additional 41 g $(MeO)_3SiH$ and 0.44 ml catalyst was added to convert the unreacted $H_2C=CHCMe_2NH_2$. Vacuum distillation provided the desired product, $(MeO)_3SiCH_2CH_2CMe_2NH_2$, at 67°/1.5 mm, with the structure confirmed by NMR.

Example 8—Utility in Fiber Glass Reinforced Composites

The product of Example 7 was compared, under identical conditions, to the industry standard 3-aminopropyltriethoxysilane (Union Carbide A-1100) is a standard glass fiber-reinforced epoxy resin composite formulation.

Physical testing showed the composite prepared with the product of Example 7 has a dry flexural strength of $97 \times 10^3$ psi and a wet flexural strength (24 hr. water boil) of $90 \times 10^3$ psi. The respective figures for A-1100 were $86 \times 10^3$ psi, and $86 \times 10^3$ psi, confirming better performance for the product of the previous example. When the silane-treated glass fibers used in preparing the above composites were compared in a 360° twist abrasion test, the A-1100-treated fibers lasted only 0.5 minutes, while fibers treated with the product of the last example lasted 1.5 minutes, showing that the product of the previous example provides improved abrasion resistance to glass fibers treated with it relative to the industry standard.

What is claimed is:

1. A process for preparing the sterically hindered aminohydrocarbylsilane of the formula $$X_3SiRCR'_2NR''_2$$

wherein
R is a linear or branched saturated or unsaturated divalent hydrocarbon group having 2 to 12 carbon atoms;
R' is an alkyl group having 1 to 8 carbon atoms or an aryl group having 6 to 12 carbon atoms;
R" is a hydrogen, an alkyl group having 1 to 8 carbon atoms, an aryl group having 6 to 12 carbon atoms, or $-SiX'_3$ wherein X' is an alkyl group having 1 to 3 carbon atoms; and
X is an alkyl group having 1 to 8 carbon atoms, an aryl group having 6 to 12 carbon atoms, and alkoxy group having 1 to 8 carbon atoms, an aryloxy group having 6 to 12 carbon atoms or a halogen atom, and
wherein each X, X', R' and R" is the same or different comprising:
reacting a silane having the formula $$X_3SiH$$

wherein X is an alkyl group having 1 to 8 carbon atoms, an aryl group having 6 to 12 carbon atoms, an alkoxy group having 1 to 8 carbon atoms, an aryloxy group having 6 to 12 carbon atoms, or a halogen atom with the proviso that the halosilane be unreactive with the sterically hindered amine group, and wherein each X is the same of different;
with a sterically hindered unsaturated amine having the formula $$R'''CR'_2NR''_2$$

wherein R' is hydrogen, an alkyl group having 1 to 8 carbon atoms or an aryl group having 6 to 12 carbon atoms;
R" is hydrogen, an alkyl group having 1 to 8 carbon atoms, an aryl group having 6 to 12 carbon atoms, or $-SiX'_3$ wherein X' is an alkyl group having 1 to 3 carbon atoms; and
R''' is an acetylenic ($-C\equiv CR''$) or vinylic ($-CH=CH_2$) group, in the presence of a noble metal catalyst at an elevated temperature.

2. A process according to claim 1, wherein R''' is $-C\equiv CH$.

3. A process according to claim 1, wherein R''' is —C≡CCH₃.

4. A process according to claim 1, wherein R''' is —C≡Cφ, wherein φ is phenyl.

5. A process according to claim 1, wherein R''' is —CH=CH₂.

6. A process according to claim 1, wherein the catalyst is a solution of chloroplatinic acid hexahydrate.

7. A process according to claim 6, wherein the solution is 4 wt % chloroplatinic acid hexahydrate dissolved in 25 to 1 parts by weight of 1,2-dimethoxyethane and 2-propanol.

8. A process according to claim 1, wherein the temperature ranges from about 50° C. to 160° C.

9. A process according to claim 8, wherein the temperature ranges from about 80° C. to 140° C.

* * * * *